US00PP17773P2

(12) United States Plant Patent
MacGregor

(10) Patent No.: US PP17,773 P2
(45) Date of Patent: May 29, 2007

(54) GRAPEVINE 'DM 8313-1'

(50) Latin Name: ***Vitis* spp hybrid**
Varietal Denomination: DM 8313-1

(76) Inventor: David W. MacGregor, 13835 51st Ave., South Haven, MN (US) 55382

( * ) Notice: Subject to any disclaimer, the term of this patent is extended or adjusted under 35 U.S.C. 154(b) by 147 days.

(21) Appl. No.: 11/048,570

(22) Filed: Jan. 31, 2005

Related U.S. Application Data

(60) Provisional application No. 60/542,215, filed on Feb. 3, 2004.

(51) Int. Cl.
*A01H 5/00* (2006.01)

(52) U.S. Cl. ..... Plt./207

(58) Field of Classification Search ..... Plt./207, Plt./205, 226

See application file for complete search history.

*Primary Examiner*—Kent Bell
*Assistant Examiner*—Annette H Para
(74) *Attorney, Agent, or Firm*—Stratton Ballew PLLC

(57) ABSTRACT

A new and distinct grapevine variety named 'DM 8313-1' is disclosed. The new variety originated from a hand pollinated cross made at South Haven, Minn., and is distinguishable by virtue of its cold hardiness in USDA Zone 4, combined with its fine muscat flavor similar to *Vitis vinifera* variety 'Muscat Blanc.'

2 Drawing Sheets

Figure 1:
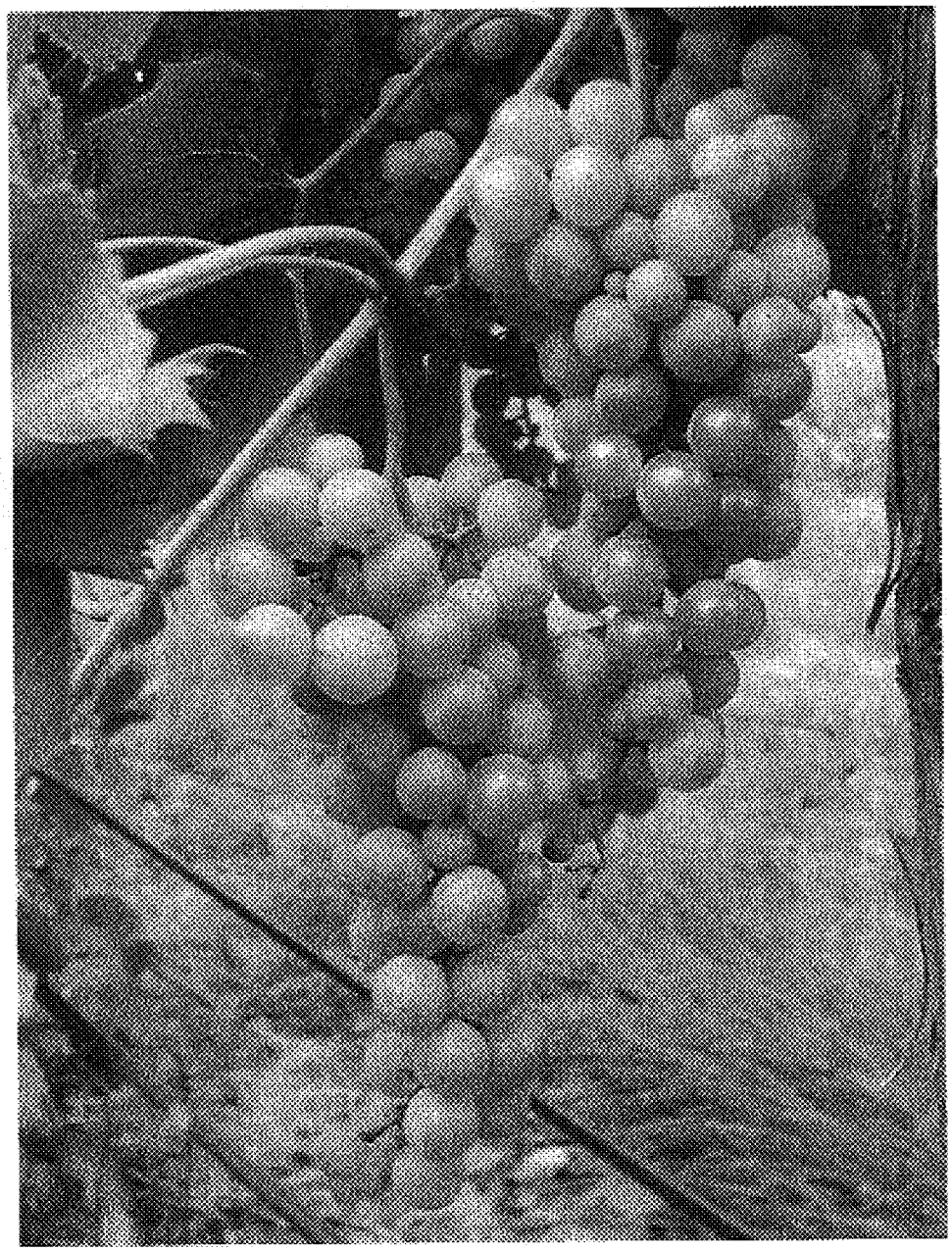

Latin name of the genus and species of the plant claimed: *Vitis* spp hybrid.
Variety denomination: 'DM 8313-1'.

BACKGROUND AND SUMMARY OF THE INVENTION

The new and distinct grapevine described and claimed herein originated from a hand-pollinated cross of 'ES 2-11-4' (unpatented) and 'DM P3-54' (unpatented). 'DM P3-54', the male parent, is a blue grape which resulted from a cross of 'Suelter' (unpatented) with the German *vinifera* variety 'Morio Muskat' (unpatented), and maintains the flavor of 'Morio Muscat' as well as much of the winter hardiness of 'Suelter'. 'ES 2-11-4', the female parent, is a white grape of French and American hybrid parentage with rather large clusters and berries having a pleasing neutral flavor and making a white wine that has been compared to Chenin Blanc. Thus the new variety is a complex hybrid with genes contributed by *V. vinifera, V. riparia,* and several other species, these having come from the at least three French hybrid varieties in the background of 'ES 2-11-4'. The cross was made in 1983 near South Haven, Minn., where the seedlings were grown out and evaluated and the new variety selected for additional testing in 1987.

In 1988 the original plant selection was propagated asexually by rooting hardwood cuttings at South Haven, Minn., and a second test planting was established. The new variety was found to root readily from hardwood cuttings and all propagules have been observed to be true to type in that the vegetative and fruit characteristics of the original plant have been maintained. Subsequently, other test plantings were made in Minnesota and at Pierce, Nebr. Nearly two decades of testing has shown considerable winter injury during cold winters at South Haven, Minn., a USDA Plant Hardiness Zone 3 location, but only light to moderate injury in zone 4B locations, similar to the 'Foch' French hybrid cultivar (unpatented). Compared to other grape cultivars of Minnesota origin, the new variety appears to be hardier than 'Swenson Red' but less hardy than 'Edelweiss'.

Vines of the new variety have been of moderate to somewhat less than moderate vigor, depending upon the growing location. 'DM 8313-1' displays the somewhat trailing growth habit typical of many French hybrid cultivars. It has tested from somewhat below average to somewhat above average in productivity compared to many other cultivars tested in several locations. The new variety is moderately resistant to most common fungus diseases of grapevines. Under the occasionally humid conditions of the Midwest it would seem to require a normal chemical disease control program to protect from downy mildew (*Uncinula necator* Burr.) which is controllable by the use of available fungicides. The fruit has shown no inclination to split following rains and hangs in good condition for late harvest. Berries adhere well to the fruit pedicel and do not shatter from the clusters during this time.

The new cultivar ripens in early midseason, about with the 'Foch' cultivar. Sugar and acid balance is good for winemaking with brix readings around 20 degrees and acid readings around 1%, these readings being considered good for grapes raised in a cool Zone 4 location. The berries are greenish yellow at harvest, weigh about 1.5 grams apiece, and are spherical in shape. Clusters are small medium in size, about 65 grams, cylindrical to conical in shape and moderately well filled but not compact. Clusters are borne two or three per shoot on medium long peduncles that are relatively easy to harvest. Grafted vines or vines grown on fertile soils have produced significantly larger clusters than the averages given here.

The new variety has a fine muscat flavor similar to *Vitis vinifera* variety 'Muscat Blanc' (unpatented), and has produced excellent wines when vinified by both amateur and professional winemakers.

BRIEF DESCRIPTION OF THE PHOTOGRAPHS

Figure 2:
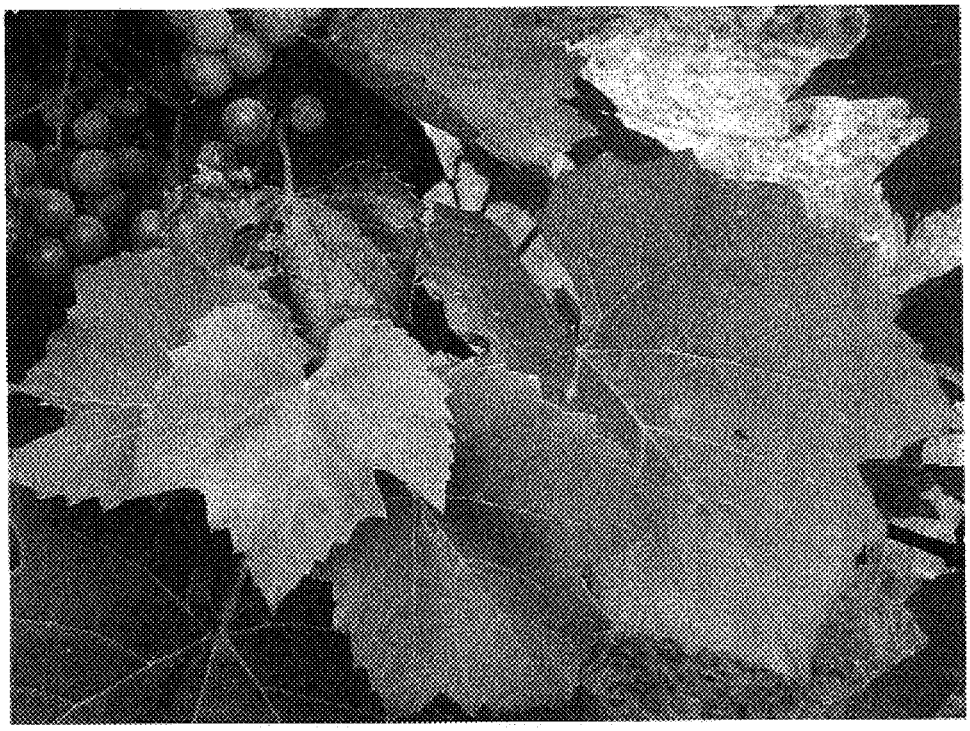

The accompanying photographs show typical specimens of the fruit (FIG. 1) and leaf (FIG. 2) of the new variety in color as nearly true as it is reasonably possible to make in a color illustration of this character.

DETAILED DESCRIPTION OF THE NEW VARIETY

The following is a detailed description of the botanical characteristics of the subject grapevine and its fruit, based on observations made near South Haven, Minn., USA, during the 2004 growing season. Color descriptions refer to The Royal Horticultural Society Colour Chart. It should be understood that the botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Vine:
   *Size.*—Average to somewhat less than average. Three year old vines at South Haven, Minn. grown on an Esterville sandy loam were on the top of a 5 ft 3 in. trellis with a trunk diameter of ½ in. at one meter from the ground.
   *Shape.*—Smooth, oval in cross section.
   *Productivity.*—Average at one site in Central Minnesota, and one site in northern Nebraska. Above average at a test location in southern Minnesota. Mature vines yielded 8.3 pounds at 5 foot spacing at South Haven, Minn. in 2003 after a winter when cold injury was common in Minnesota vineyards.
   *Canes.*—Slightly less than medium in diameter; somewhat spreading in growth habit.
   *Density of foliage.*—Medium.
   *Color.*—New bark greyed orange 177B; old bark brown N200B.
2. Time of bud burst: Medium (about the same as 'Grenache Noir N').
3. Young shoot:
   *Openness of tip.*—Slightly open; Density of prostrate hairs on tip — dense; Anthocyanin coloration of prostrate hairs on tip — absent or very weak.
4. Young leaf:
   *Color of upper side of blade.*—Yellow green 144C with anthocyanin spots; Density of prostrate hairs between main veins on lower side of blade — dense; Density of erect hairs on main veins on lower side of blade — sparse.
5. Shoot:
   *Attitude* (*before tying*).—Semi-erect; Color of dorsal side of internode (well illuminated) — green with red stripes; Color of ventral side of internode (without direct sunlight) — completely green; Density of erect hairs on internodes — sparse; Number of consecutive tendrils — less than three; Length of tendril — 7.6 to 12.7 cm, similar to 'Pinot noir N'.
6. Flower:
   *Sexual organs.*—Fully developed stamens and fully developed gynoecium.
   *Quantity.*—2 to 3 inflorescences per shoot; 70 to 110 flowers per cluster.
   *Length of flower cluster.*—9.5 to 14.6 cm.
   *Pedicel.*—Length 0.2 to 0.3 cm.
7. Mature leaf:
   *Size of blade.*—Small, width 14 cm, length 10 cm; Shape of blade — deltoid; Profile in cross section — V-shaped; Blistering of upper side of blade — weak; Color of upper side — yellow green 146A; Color of lower side — yellow green 146B; Number of lobes — none; Depth of upper lateral sinuses — very shallow; Arrangement of lobes of upper lateral sinuses — open; Arrangement of lobes of petiole sinus — half open; Petiole sinus limited by veins — absent; Length of teeth — medium, 0.1 to 1.0 cm; Ratio length/width of teeth — length approximately same as width; Shape of teeth — both sides straight; Anthocyanin coloration of main veins on upper side of blade — absent or very weak; Density of prostrate hairs between main veins on lower side of blade — sparse; Density of erect hairs on main veins on lower side of blade — dense; Length of petiole compared to middle vein — much shorter.
8. Time of beginning of berry ripening — September 5 to September 20, shortly before 'Marichel Foch'.
9. Berry cluster:
   *Size* (*peduncle excluded*).—Small, approximately 65 g, width 6 cm, length 14 cm; Density — loose; Peduncle length 9.5 to 14.6 cm.; Peduncle color yellow green 146C; Pedicel length 0.2 to 0.3 cm; Pedicel color greyed brown N199A.
10. Berry:
   *Size.*—Small, approximately 1.5 g, diameter 14 mm; Shape in profile — circular; Color of skin (without bloom) — yellow-green 148A, changing to yellow green 152D as the berry ripens; Ease of detachment from pedicel — relatively easy; Thickness of skin — thin; Anthocyanin coloration of flesh — absent or very weak; Color of flesh — yellow-green 148A; Firmness of flesh — soft; Juiciness of flesh — very juicy; Flavor — muscat; Seeds — formation complete, length 0.5 to 0.6 cm, width 0.3 to 0.4 cm, color greyed-orange 166C.
11. Woody shoot:
   *Main color* (*without bloom*).—Yellowish brown; Relief of surface — smooth.

I claim:

1. A new and distinct grapevine substantially as illustrated and described herein.

* * * * *